US00PP14049P29

(12) United States Plant Patent
Dümmen

(10) Patent No.: US PP14,049 P2
(45) Date of Patent: Aug. 5, 2003

(54) GERANIUM PLANT NAMED 'DUEVICORAL'

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 10/228,463

(22) Filed: Aug. 27, 2002

(51) Int. Cl.[7] ..... A01H 5/00
(52) U.S. Cl. ..... Plt./327
(58) Field of Search ..... Plt./327

*Primary Examiner*—Kent Bell
(74) *Attorney, Agent, or Firm*—C. A. Whealy

(57) ABSTRACT

A new and distinct cultivar of Zonal Geranium plant named 'Duevicoral', characterized by its upright, outwardly spreading and rounded plant habit; freely branching habit; freely flowering habit; and orange red-colored flowers.

1 Drawing Sheet

BOTANICAL CLASSIFICATION/CULTIVAR DENOMINATION

*Pelargonium×hortorum* cultivar 'Duevicoral'.

BACKGROUND OF THE INVENTION

The present invention relates to a new and distinct cultivar of Zonal Geranium plant, botanically known as *Pelargonium×hortorum*, and hereinafter referred to by the name 'Duevicoral'.

The new Zonal Geranium is a product of a planned breeding program conducted by the Inventor in Rheinberg, Germany. The objective of the breeding program was to develop new Zonal Geraniums with attractive flower and foliage colors.

The new Zonal Geranium originated from a cross-pollination made by the Inventor in June, 1998, of a proprietary selection of *Pelargonium×hortorum* identified as code number F-13-09, not patented, as the female, or seed, parent with a proprietary selection of *Pelargonium× hortorum* identified as code number F-20- 15, not patented, as the male, or pollen, parent. The cultivar Duevicoral was discovered and selected by the Inventor as a flowering plant within the progeny from this cross in a controlled environment in Rheinberg, Germany in June, 2001.

Asexual reproduction of the new cultivar by terminal vegetative cuttings taken at Rheinberg, Germany since June, 2001, has shown that the unique features of this new Zonal Geranium are stable and reproduced true to type in successive generations of asexual reproduction.

SUMMARY OF THE INVENTION

The following traits have been repeatedly observed and are determined to be the unique characteristics of 'Duevicoral'. These characteristics in combination distinguish 'Duevicoral' as a new cultivar and distinguish it from other known Zonal Geranium cultivars:

1. Upright, outwardly spreading and rounded plant habit.
2. Freely branching habit.
3. Freely flowering habit.
4. Orange red-colored flowers.

Compared to plants of the female parent, the selection F-13-09, plants of the new Zonal Geranium differ in flower color. Compared to plants of the male parent, the selection F-20-15, plants of the new Zonal Geranium are more vigorous.

The new Zonal Geranium can be compared to plants of the cultivar 'HWD Ventura', disclosed in U.S. plant Pat. No. 9,747. In side-by-side comparisons conducted in Rheinberg, Germany, plants of the new Zonal Geranium differed from plants of the cultivar HWD Ventura in the following characteristics:

1. Plants of the new Zonal Geranium were taller than plants of the cultivar HWD Ventura.
2. Plants of the new Zonal Geranium had broader leaves than plants of the cultivar HWD Ventura.
3. Leaves of plants of the new Zonal Geranium did not have a zonation pattern whereas leaves of plants of the cultivar HWD Ventura had a zonation pattern.
4. Plants of the new Zonal Geranium had more flowers per umbel than plants of the cultivar HWD Ventura.
5. Plants of the new Zonal Geranium had shorter pedicels than plants of the cultivar HWD Ventura.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal Geranium. The photograph comprises a side perspective view of typical flowering plants of 'Duevicoral' grown in a container.

DETAILED BOTANICAL DESCRIPTION

The cultivar Duevicoral has not been observed under all possible environmental conditions. The phenotype may vary somewhat with variations in environment, such as temperature and light intensity, without, however, any variance in genotype.

The aforementioned photograph, following observations and measurements describe plants grown in Rheinberg, Germany during the summer under commercial practice in a glass-covered greenhouse with day and night temperatures about 18° C. and light levels about 4,500 foot-candles. Plants were grown in 10.5-cm containers. Plants were about eight weeks from unrooted cuttings when the photograph and the detailed botanical description were taken.

In the following description, color references are made to The Royal Horticultural Society Colour Chart, 1995 edition, except where general terms of ordinary dictionary significance are used.

Botanical classification:

*Pelargonium×hortorum* cultivar Duevicoral, also known as 298-7452-02.

Parentage:

*Female parent.*—Proprietary selection of *Pelargonium×hortorum* identified as F-3-09, not patented.

*Male parent.*—Prorietary selection of *Pelargonium×hortorum* identified as F-20-15, not patented.

Propagation:

*Type cutting.*—Terminal vegetative cuttings.

*Time to initiate roots.*—Summer: About 5 days at 20° C. Winter: About 7 days at 20° C.

*Time to develop roots.*—Summer: About 21 days at 20° C. Winter: About 28 days at 20° C.

*Root description.*—Fine, fibrous; white in color.

*Rooting habit.*—Freely branching.

Plant description:

*General appearance.*—Upright, outwardly spreading and rounded plant habit; densely foliated.

*Growth and branching habit.*—Moderately vigorous. Basal branching, about three lateral branches per plant.

*Plant height.*—About 26 cm.

*Plant width.*—About 22 cm.

*Lateral branches.*—Length: About 12 cm. Internode length: About 2 cm. Texture: Smooth. Color: 144A.

*Foliage description.*—Arrangement: Alternate, single. Quantity of leaves per lateral branch: About six. Length: About 7.9 cm. Width: About 9.2 cm. Shape: Orbicular. Apex: Rounded. Base: Cordate. Margin: Crenate. Venation pattern: Palmate. Texture, upper and lower surfaces: Pubescent. Color: Young and fully expanded foliage, upper surface: 137B. Young and fully expanded foliage, lower surface: 138B. Venation, upper and lower surfaces: 144B. Zonation pattern: Not observed. Petiole: Length: About 5.9 cm. Diameter: About 3 mm. Color, upper and lower surfaces: 144A.

Flower description:

*Flower arrangement.*—Orange red-colored semi-double flowers arranged in rounded hemispherical umbels arising from apical leaf axils. Umbels displayed above and beyond the foliage on peduncles. Flowers rounded in form. Umbels persistent, flowers not persistent. Flowers not fragrant.

*Ouantity of flowers.*—Freely flowering; at full flower, plants have about six open and developing umbels with about 30 to 35 flowers per umbel.

*Flowing season.*—Flowering continuous spring until the autumn.

*Flower longevity.*—Flowers last about two weeks on the plant.

*Umbel size.*—Height: About 6.5 cm. Diameter: About 11 cm.

*Flower size.*—Diameter: About 4.7 cm. Depth (height): About 1.7 cm.

*Flower buds.*—Length: About 1.2 cm. Diameter: About 7 mm. Shape: Ovoid. Color: 144A.

*Petals.*—Quantity per flower: About five. Length: About 2.5 cm. Width: About 1.9 cm. Shape: Obovate. Apex: Rounded. Base: Attenuate. Margin: Entire; sinuate. Texture, upper and lower surfaces: Smooth. Color: When opening and fully opened, upper surface: 41A. When opening and fully opened, lower surface: 41B to 41C.

*Petaloids.*—Quantity per flower: About three. Length: About 2 cm. Width: About 1.5 cm. Shape: Obovate. Apex: Rounded. Base: Attenuate. Margin: Entire; sinuate. Texture, upper and lower surfaces: Smooth. Color: When opening and fully opened, upper surface: 41A. When opening and fully opened, lower surface: 41B to 41C.

*Sepals.*—Quantity per flower: Five, arranged in a single whorl. Length: About 1 cm. Width: About 3 mm. Shape: Elongated, tapering. Apex: Apiculate. Margin: Entire. Texture, upper and lower surfaces: Smooth; glabrous. Color, upper and lower surfaces: 144A.

*Peduncle* (*umbel stem*).—Length: About 20.7 cm. Diameter: Less than 1 cm. Angle: Mostly erect. Strength: Moderately strong. Texture: Pubescent. Color: 144A.

*Pedicel* (*individual flower stem*).—Length: About 2.9 cm. Diameter: About 1 mm. Angle: Mostly erect. Strength: Moderately strong. Texture: Pubescent. Color: 144A faintly overlain with 59B.

*Reproductive organs.*—Androecium: Anther quantity per flower: About six. Anther length: About 2 mm. Anther shape: Ovate. Anther color: 45D. Pollen amount: Moderate. Pollen color: 25A. Gynoecium: Pistil quantity per flower: One. Pistil length: About 1 cm. Stigma shape: Five-parted, star-shaped. Stigma color: 53A. Style length: About 5 mm. Style color: 53B. Ovary color: 144A.

*Seed/fruit.*—Development of seeds and fruit have not been observed.

Disease/pest resistance: Plants of the new Zonal Geranium have not been observed to be resistant to pathogens and pests common to Zonal Geraniums.

Temperature tolerance: Plants of the new Zonal Geranium have been observed to be tolerant to temperatures ranging from 5 to 40° C.

It is claimed:

1. A new and distinct cultivar of Zonal Geranium plant named 'Duevicoral', as herein illustrated and described.

* * * * *

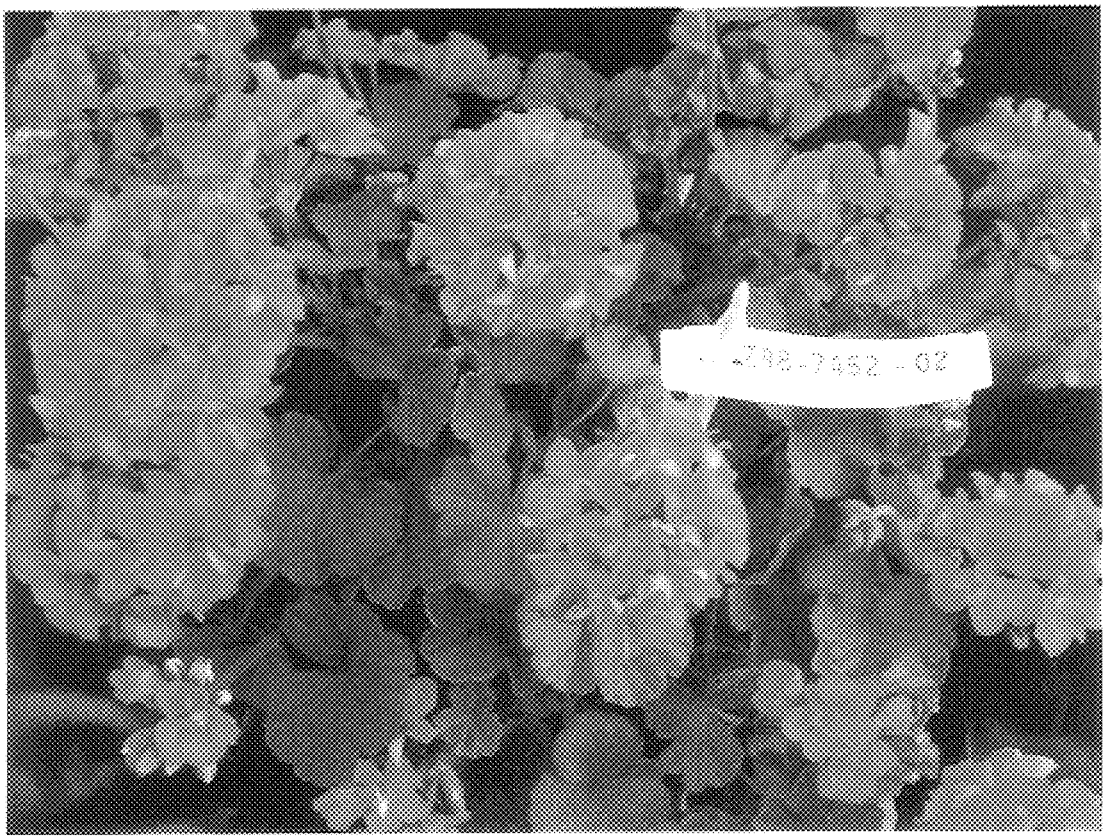
298-7452-02